(12) United States Patent
Callaway

(10) Patent No.: US 7,406,967 B2
(45) Date of Patent: Aug. 5, 2008

(54) UNIVERSAL INTRAVENOUS ARM SUPPORT

(76) Inventor: James J. Callaway, 615 Woodleigh Dr., Nashville, TN (US) 37215-1126

( * ) Notice: Subject to any disclaimer, the term of this patent is extended or adjusted under 35 U.S.C. 154(b) by 703 days.

(21) Appl. No.: 10/770,533

(22) Filed: Feb. 4, 2004

(65) Prior Publication Data

US 2004/0154628 A1   Aug. 12, 2004

Related U.S. Application Data

(60) Provisional application No. 60/444,945, filed on Feb. 5, 2003.

(51) Int. Cl.
  *A61F 5/37*   (2006.01)
  *A61F 5/00*   (2006.01)
(52) U.S. Cl. .................... 128/877; 128/878; 128/879; 128/DIG. 6; 602/20; 602/21; 602/22
(58) Field of Classification Search ......... 128/877–879, 128/DIG. 6; 602/20–22
See application file for complete search history.

(56) References Cited

U.S. PATENT DOCUMENTS

| D170,885   S   | 11/1953  | Neville |
| 2,693,794  A   | 11/1954  | Neville |
| 2,744,526  A   | 5/1956   | Saylors |
| 3,295,518  A * | 1/1967   | Hazlewood et al. ......... 128/877 |
| 3,722,508  A   | 3/1973   | Roberts |
| 3,724,456  A   | 4/1973   | Waxman |
| 3,812,851  A   | 5/1974   | Rodriguez |
| 3,815,588  A * | 6/1974   | Klausner ...................... 602/4 |
| 4,502,477  A   | 3/1985   | Lewis |
| 4,862,904  A * | 9/1989   | West et al. .................. 128/877 |
| 5,018,534  A * | 5/1991   | Grant ......................... 128/877 |
| 5,025,801  A * | 6/1991   | Callaway .................... 128/877 |
| 5,263,497  A * | 11/1993  | Grabenkort et al. ......... 128/877 |
| 5,845,643  A * | 12/1998  | Vergano et al. ............. 128/877 |

* cited by examiner

*Primary Examiner*—Patricia Bianco
*Assistant Examiner*—Tarla Patel
(74) *Attorney, Agent, or Firm*—Jacobson Holman PLLC

(57) ABSTRACT

An arm board for supporting the forearm, wrist and hand during IV therapy which includes a contoured brace with removable straps for securing the forearm and middle two fingers of the patient's hand to the support, allowing some limited movement of the middle two fingers, and free movement of the little finger, thumb and index finger to reduce fatigue without altering the position of the IV tubing.

5 Claims, 3 Drawing Sheets

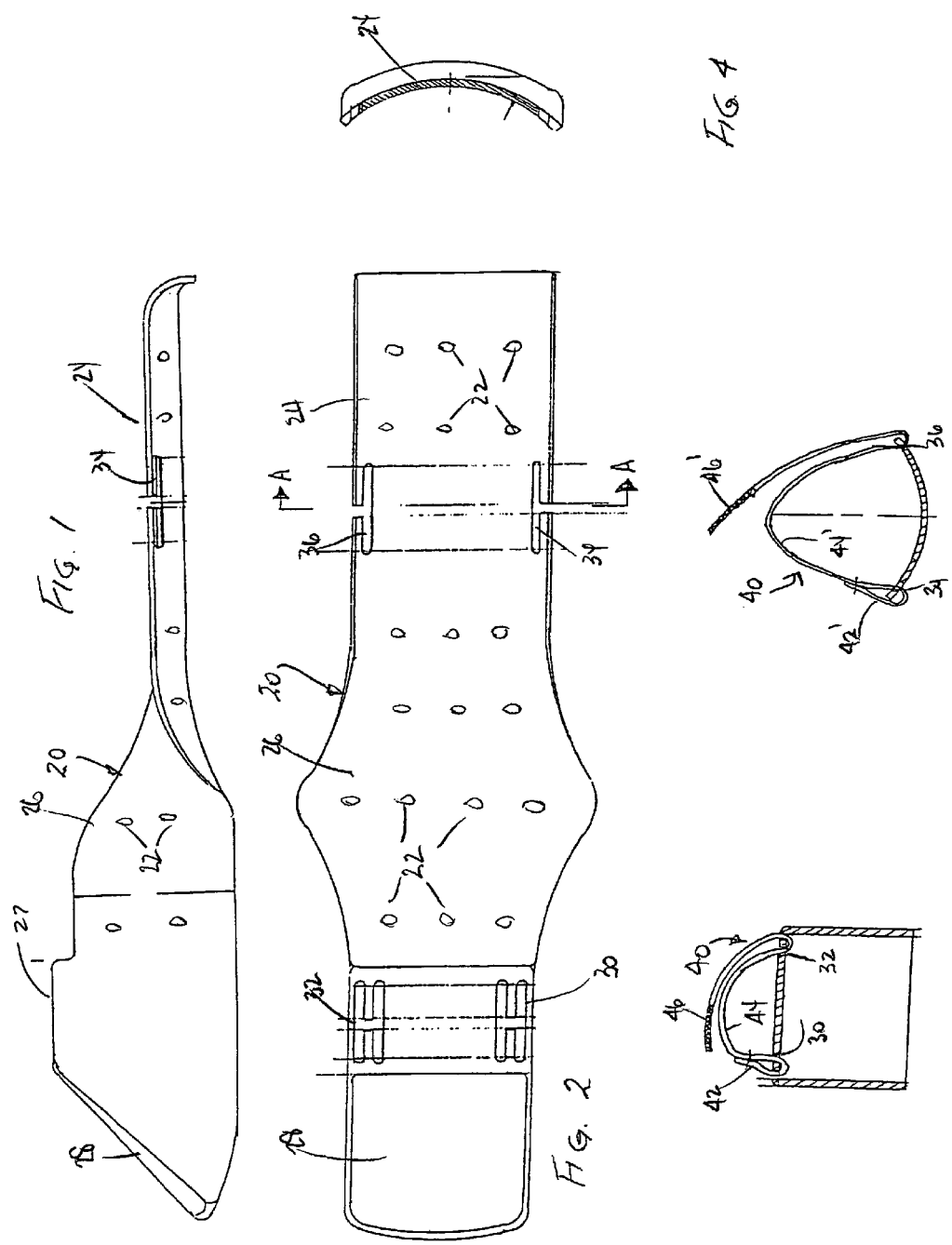

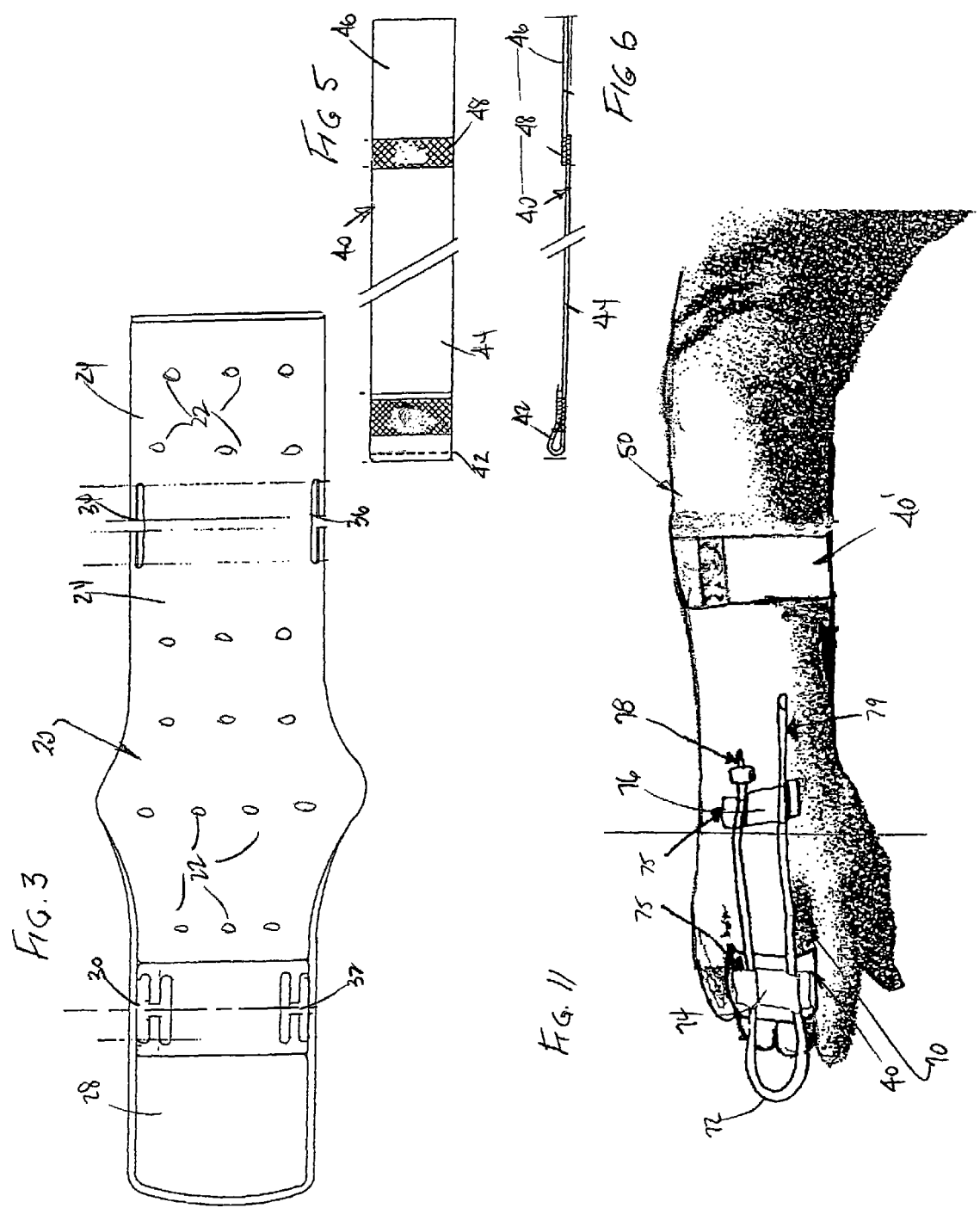

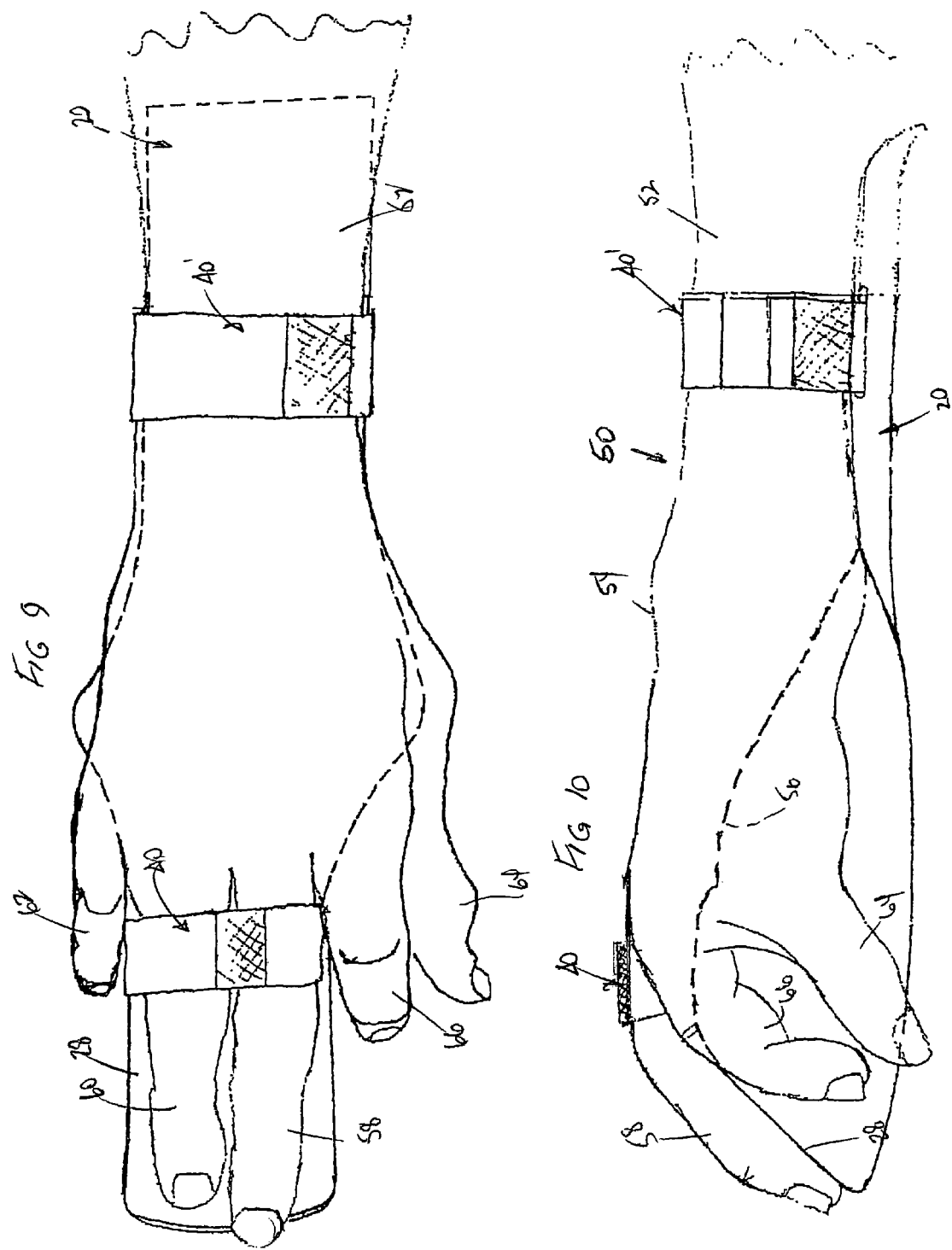

UNIVERSAL INTRAVENOUS ARM SUPPORT

This application claims priority from and the benefit of U.S. Provisional Application Ser. No. 60/444,945, filed on Feb. 5, 2003.

BACKGROUND OF THE INVENTION

1. Field of the Invention

This invention relates generally to an arm board or arm rest for supporting the forearm, wrist and hand of a patient during intravenous therapy.

2. Discussion of the Related Art

In intravenous (IV) therapy, a needle attached to a tube connected to an IV bag is typically placed in a vein of the patient proximate a limb joint such as the elbow where the veins are closer to the skin and more accessible, and infusion, transfusion, phlebotomy or other procedures or therapies are performed by drawing or passing fluids through the tube. It is desirable in many instances to support the limb proximal its joint at the IV site.

Previously, this was accomplished by simply placing a short board or splint along the limb, and then securing the limb to the splint board as with tape, and the IV tubing might either be simply taped down along a portion of the patient's arm or otherwise made fast to the splint in order to prevent any movement of the IV needle in the vein or possible displacement of the IV needle from the vein. Such techniques often resulted in discomfort to the patient due to the non-conformability of the splint board with the patient's forearm and hand.

Various types of prior art supports, immobilizers and restraints have been proposed for use in association with IV therapy in lieu of the splint board, some of which are shown in U.S. Pat. No. 2,693,794 and U.S. Design Patent No. 170,885 to Nevill, U.S. Pat. No. 3,724,456 to Waxman, U.S. Pat. No. 3,722,508 to Roberts, U.S. Pat. No. 3,812,851 to Rodriguez, U.S. Pat. No. 2,744,526 to Saylors and U.S. Pat. No. 4,502,477 to Lewis, each of which had disadvantages, either due to the discomfort to the patient or the difficulty and expense in manufacture.

An improvement to the prior art devices is seen in my prior patent No. 5,025,801 which included a contoured support having adjoined forearm, wrist and hand support surfaces for conformally supporting the ventral surfaces of the forearm, wrist and palm of a patient. A hand grip was provided adjoining the palm support surface, and thumb recesses were provided on each side of the hand support to enable the patient to grip the support. A tubing support member was pivotally mounted at the hand grip to provide support for IV tubing, the tubing support being pivotable about its hand grip mounting, as well as vertically adjustable with respect to the hand grip, with locking or clamping mechanisms manually operable for fixing the tubing support in place. While this device had certain advantages over prior art IV arm supports, it was somewhat cumbersome and difficult to use and never received widespread acceptance.

SUMMARY OF THE INVENTION

It is a primary object of this invention to provide a universal IV arm support which is simple and inexpensive to manufacture, yet adapted to accommodate both right and left forearms and hands in a comfortable and secure manner.

Another object of this invention is to provide an IV arm support which permits free movement of the little finger and of the thumb and index finger of the immobilized hand, allowing grasping between the latter two digits.

A further object of this invention is the provision of an arm board for supporting the forearm, wrist and hand during IV therapy which includes a contoured brace with removable straps for securing the forearm and middle two fingers of the patient's hand to the support, allowing some limited movement of the middle two fingers, and free movement of the little finger, thumb and index finger to reduce fatigue without altering the position of the IV tubing.

A still further object of this invention is the provision of an inexpensive, one piece, molded plastic, universal IV arm support, with readily attachable and detachable forearm and finger straps, enabling the support to be reused, if desired, or disposed of after use if contaminated.

Additional features and advantages of the invention will become apparent from the ensuing description and claims read in conjunction with the attached drawings.

BRIEF DESCRIPTION OF THE DRAWINGS

The accompanying drawings, which are included to provide a further understanding of the invention and are incorporated in and constitute a part of this specification and, together with the description, serve to explain the principles of the invention.

FIG. 1 is side elevational view of a universal IV arm support member according to the instant inventive concepts;

FIG. 2 is a top plan view thereof;

FIG. 3 is a bottom plan view thereof;

FIG. 4 is a transverse cross-sectional view taken along line A-A of FIG. 2;

FIG. 5 is an elevational view, partially broken away for illustrative convenience, illustrating a flexible strap for use in conjunction with the arm support member of this invention;

FIG. 6 is a side elevational view of the strap of FIG. 5;

FIG. 7 is a transverse cross-sectional view through the arm support member of this invention showing the manner in which a strap is inserted to secure the middle and ring fingers of a patient thereto;

FIG. 8 is a similar view showing the manner in which a strap is installed for securing the forearm of a patient to the arm support member of this invention;

FIG. 9 is a top plan view showing a patient's forearm and hand fixed to an arm support according to this invention;

FIG. 10 is a side elevational view thereof; and

FIG. 11 is a view similar to FIG. 9, but schematically showing the manner in which the needle and tubing from an IV fluid bag would be taped to a patient's hand attached to an arm support according to this invention.

Like reference characters refer to like parts throughout the several views of the drawings.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Referring particularly to FIGS. 1-4, an integral universal IV arm support member according to this invention is designated generally by the reference numeral 20 and comprises basically a single molded plastic element contoured to fit the forearm, wrist and middle fingers of a patient. The member 20 may be formed of any conventional plastic according to well known molding techniques. Perforations 22 through the arm support member 20 may be provided to permit the free flow of air therethrough in use.

As seen in FIGS. 9-11, when a patient's arm 50 is placed on the support 20, the forearm 52 of a patient rests in a first arcuate portion 24 of the arm support member 20 (see, particularly, FIG. 4), the wrist 54 and palm 56 resting on a second gently, upwardly inclined portion 26 which rises from the first arcuate portion 24 of the arm support 20 at an angle in the range of approximately 20-40°, and preferably at an angle of approximately 30°. The middle and ring fingers 58, 60 rest on a third flat plateau 27 extending parallel to the first portion 24 and continue onto a fourth downwardly inclined portion 28 of the support member 20. The downwardly inclined portion extends from the plateau 27 at an angle in the range of approximately 40-50°, and preferably at an angle of approximately 45°. The little finger 62 is freely movable on one side of the inclined portion 28 and the thumb 64 and index finger 66 are freely moveable on the other side of the inclined portion 28 of the support member 20, allowing grasping by these members as seen in FIG. 9 and FIG. 10.

The support member 20 is contoured to fit the forearm, wrist and fingers of either the right arm and hand or the left arm and hand of most patients in a comfortable and secure manner, while permitting maximum flexibility and movement of the patient's hand and fingers to reduce fatigue, increase comfort and decrease nursing time required to administer IV fluids.

In order to secure the patient's arm to the support member 20, a pair of flexible straps of any conventional material may be provided. One such strap is shown in FIGS. 5 and 6 at 40 as including a heat-welded loop 42 at one end. A first section 44 may be of standard hook or loop construction with a cooperating loop or hook section 46 heat-welded at 48 to the opposite end.

A relatively shorter strap element 40 is shown in FIG. 7 as having the loop 42 removably engaged in a first H-shaped cutout 30 in the support member 20, with the opposite end of the strap 40 looped through a second H-shaped cutout 32 and adjustably secured over the middle and ring fingers 58, 60 of a patient's hand by the hook and loop attachment 44, 46 as seen in FIGS. 9-11. A longer strap, designated as 40', is engaged through T-shaped cutouts 34, 36 in the support arm 20 as seen in FIG. 8 to secure the patient's forearm 54 to the support arm 20.

Referring now to particularly FIG. 11, it will be seen how the tubing 70, 79 from an IV fluid bag (not shown) may be looped around at 72 and taped at 74 to the strap 40, and taped again at 75, 76 adjacent the entry of the IV needle 78 into the patient's vein.

It will now be seen that the present invention provides a simply unitary molded plastic support member that is contoured to comfortably underly the forearm, wrist and middle fingers of a patient's arm with removable, adjustable, flexible straps to secure the patient's forearm and two middle fingers to the support providing free movement of the little and index fingers and the thumb and limited movement of the middle and ring fingers, while enabling a needle and tubing attached to an IV fluid bag to be taped securely to the patient. The IV arm support of this invention is universal and simple and inexpensive to manufacture and use.

The foregoing descriptions and drawings should be considered as illustrative only of the principles of the invention. As noted, the invention may be configured in a variety of shapes and sizes and is not limited by the dimensions of the preferred embodiment. Numerous applications of the present invention will readily occur to those skilled in the art. Therefore, it is not desired to limit the invention to the preferred embodiments or the exact construction and operation shown and described. Rather, all suitable modifications and equivalents maybe resorted to as falling within the scope of the invention.

I claim:

1. An arm support for supporting the forearm, wrist, hand and only two fingers of a patient during intravenous therapy, said arm support comprising:
   a support body for supporting either a left arm and hand or a right arm and hand of the patient, said support body including
   a first portion adapted for supporting a forearm of a patient,
   a second portion extending upwardly at an angle in a range of approximately 20 to 40 degrees with respect to said first portion, said second portion supporting a wrist and a palm of one hand of the patient,
   a third portion connected to the second portion, said third portion extending generally parallel to said first portion and adapted for supporting a portion of only the two middle fingers of the patient, and
   a fourth portion extending downwardly from the third portion at an angle in a range of approximately 40 to 50 degrees, said fourth portion being of a width adapted for supporting the tips of only the two middle fingers of the patient.

2. The arm support as claimed in claim 1, wherein said first portion, said second portion, said third portion and said fourth portion are integral and fixed relative to each other to form said support body.

3. The arm support as claimed in claim 1, wherein said first portion and said third portion include a securing device for stabilizing the arm and fingers of the patient.

4. The arm support as claimed in claim 3, wherein said securing device is a strap.

5. The arm support as claimed in claim 1, wherein two sides of said third portion and said fourth portion extend to a bottom edge continuous with a bottom edge of said fourth portion.

* * * * *